(12) United States Patent
Jin et al.

(10) Patent No.: US 8,228,681 B2
(45) Date of Patent: Jul. 24, 2012

(54) PRINTED CIRCUIT BOARD AND PROBE THEREWITH

(75) Inventors: Gil Ju Jin, Seoul (KR); Jung Lim Park, Seoul (KR); Jae Yk Kim, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 324 days.

(21) Appl. No.: 12/607,571

(22) Filed: Oct. 28, 2009

(65) Prior Publication Data
US 2010/0103637 A1    Apr. 29, 2010

(30) Foreign Application Priority Data

Oct. 29, 2008  (KR) .......................... 10-2008-0106259

(51) Int. Cl.
*H05K 7/00* (2006.01)
(52) U.S. Cl. ........................................ 361/777; 361/760
(58) Field of Classification Search .................. 361/777, 361/760, 749
See application file for complete search history.

(56) References Cited

U.S. PATENT DOCUMENTS

| 5,810,009 A * | 9/1998 | Mine et al. ..................... 600/459 |
| 6,736,779 B1 * | 5/2004 | Sano et al. ..................... 600/447 |
| 7,745,976 B2 * | 6/2010 | Cerofolini ..................... 310/334 |

* cited by examiner

*Primary Examiner* — Yuriy Semenenko
(74) *Attorney, Agent, or Firm* — McDermott Will & Emery LLP

(57) ABSTRACT

Disclosed herein are a printed circuit board (PCB) and a probe including the same. The probe includes a transducer, a PCB having a pattern part contacting the transducer via face-to-face contact, and a bonding member bonding the transducer to the pattern part of the PCB. The bonding part of the PCB is provided with the pattern part to increase a bonding area of the bonding part and to allow the bonding member to contact not only a metal layer of the bonding part but also an electrical insulation part thereof, thereby improving a bonding force between the transducer and the PCB. As a result, the transducer can be reliably bonded to the PCB, so that performance of the transducer can be prevented from being deteriorated due to defective connection between the PCB and the transducer.

4 Claims, 8 Drawing Sheets

PRINTED CIRCUIT BOARD AND PROBE THEREWITH

CROSS-REFERENCE TO RELATED APPLICATIONS

This application claims the benefit of Korean Patent Application No. 10-2008-0106259, filed on Oct. 29, 2008, the entire contents of which are incorporated by reference herein.

BACKGROUND OF THE INVENTION

1. Field of the Invention

The present invention relates to a printed circuit board (PCB) and, more particularly, to a PCB and a probe including the same for use in an ultrasound system that generates internal images of a patient body with ultrasound waves.

2. Description of the Related Art

Generally, an ultrasound system refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal). The ultrasound system has been widely used for diagnosis of the heart, the abdomen, the urinary organs, and in obstetrics and gynecology due to various merits such as small size, low price, real-time image display, and high stability through elimination of any radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

Particularly, the ultrasound system includes a probe which transmits an ultrasound signal to a patient body and receives the ultrasound echo-signal reflected therefrom to obtain the ultrasound image of the patient body.

The probe includes a transducer, a case with an open upper end, a cover coupled to the open upper end of the case to directly contact the body surface of the patient, and the like.

The transducer includes a piezoelectric layer in which a piezoelectric material converts electrical signals into sound signals or vice versa while vibrating, a coordination layer reducing a difference in sound impedance between the piezoelectric layer and a patient body to allow as much of the ultrasound waves generated from the piezoelectric layer to be transferred to the patient body as possible, a lens layer focusing the ultrasound waves, which travel in front of the piezoelectric layer, onto a predetermined point, and a backing layer blocking the ultrasound waves from traveling in a rearward direction of the piezoelectric layer to prevent image distortion.

The piezoelectric layer includes a piezoelectric device, and signal and ground electrodes provided to upper and lower ends of the piezoelectric device, respectively. Further, a PCB is bonded to the piezoelectric layer to be connected to the signal and ground electrodes in such a way that a bonding surface of the PCB is bonded to the ground electrode by an adhesive.

In such a probe, a bonding force between the piezoelectric device and the bonding surface of the PCB is low to cause unreliable bonding between the PCB and the piezoelectric layer, thereby deteriorating performance of the probe. Therefore, there is a need for an improved probe that overcomes such a problem.

SUMMARY OF THE INVENTION

The present invention is conceived to solve the problem of the conventional technique as described above, and an aspect of the present invention is to provide an improved probe that can prevent deterioration of performance caused by defective connection between a piezoelectric layer and a printed circuit board (PCB).

In accordance with an aspect of the present invention, a probe includes: a transducer; a PCB having a pattern part contacting the transducer via face-to-face contact; and a bonding member bonding the transducer to the pattern part of the PCB.

The pattern part may include at least one of a polygonal pattern, a transverse line pattern, a lengthwise line pattern, an oblique line pattern, a circular pattern, an elliptical pattern, and a wave pattern.

The pattern part may include a convex portion.

The pattern part may include a concave portion.

In accordance with another aspect of the present invention, a PCB includes: a bonding part contacting an object via face-to-face contact; and a pattern part provided to the bonding part.

The pattern part may include at least one of a polygonal pattern, an oblique line pattern, a transverse line pattern, a lengthwise line pattern, a circular pattern, an elliptical pattern, and a wave pattern.

BRIEF DESCRIPTION OF THE DRAWINGS

The above and other aspects, features and advantages of the present invention will become apparent from the following description of exemplary embodiments given in conjunction with the accompanying drawings, in which.

DETAILED DESCRIPTION OF THE EMBODIMENT

Exemplary embodiments of the present invention will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the present invention into account and can be changed according to the custom or intention of users or operators. Therefore, definition of the terms should be made according to overall disclosures set forth herein.

Figure 1:
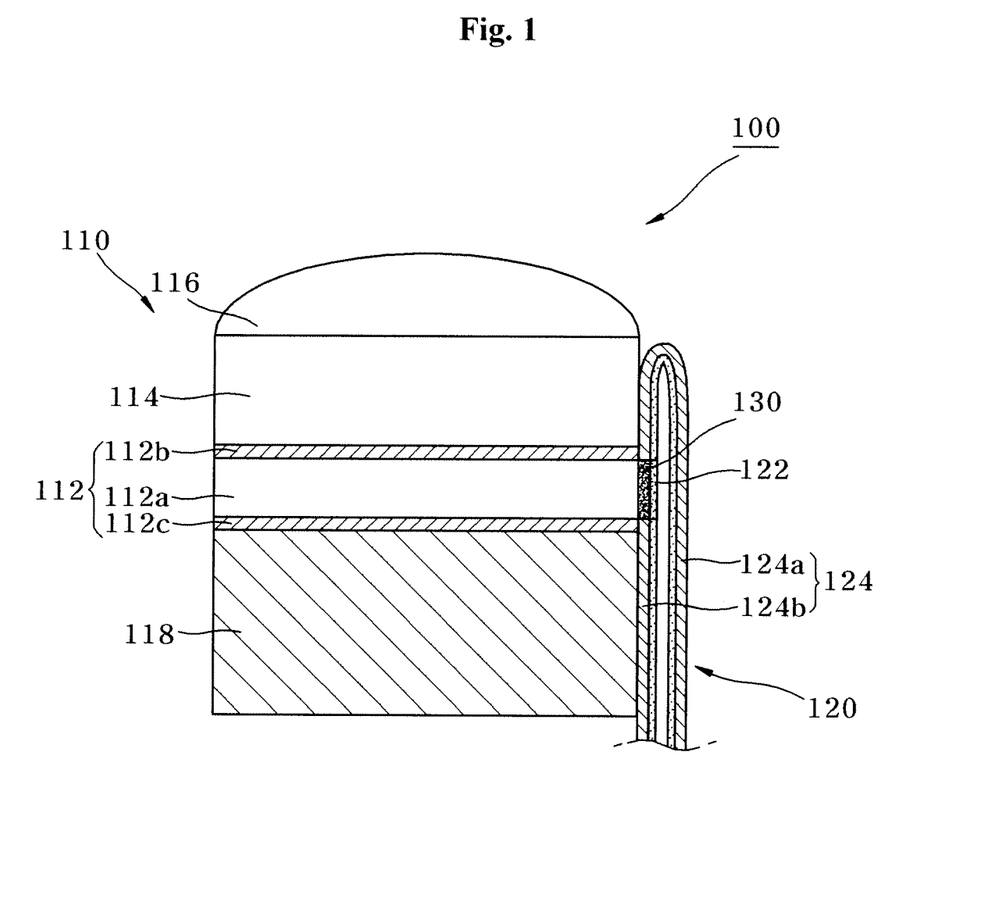
FIG. 1 is a schematic cross-sectional view of a probe according to an embodiment of the present invention.
Figure 2:
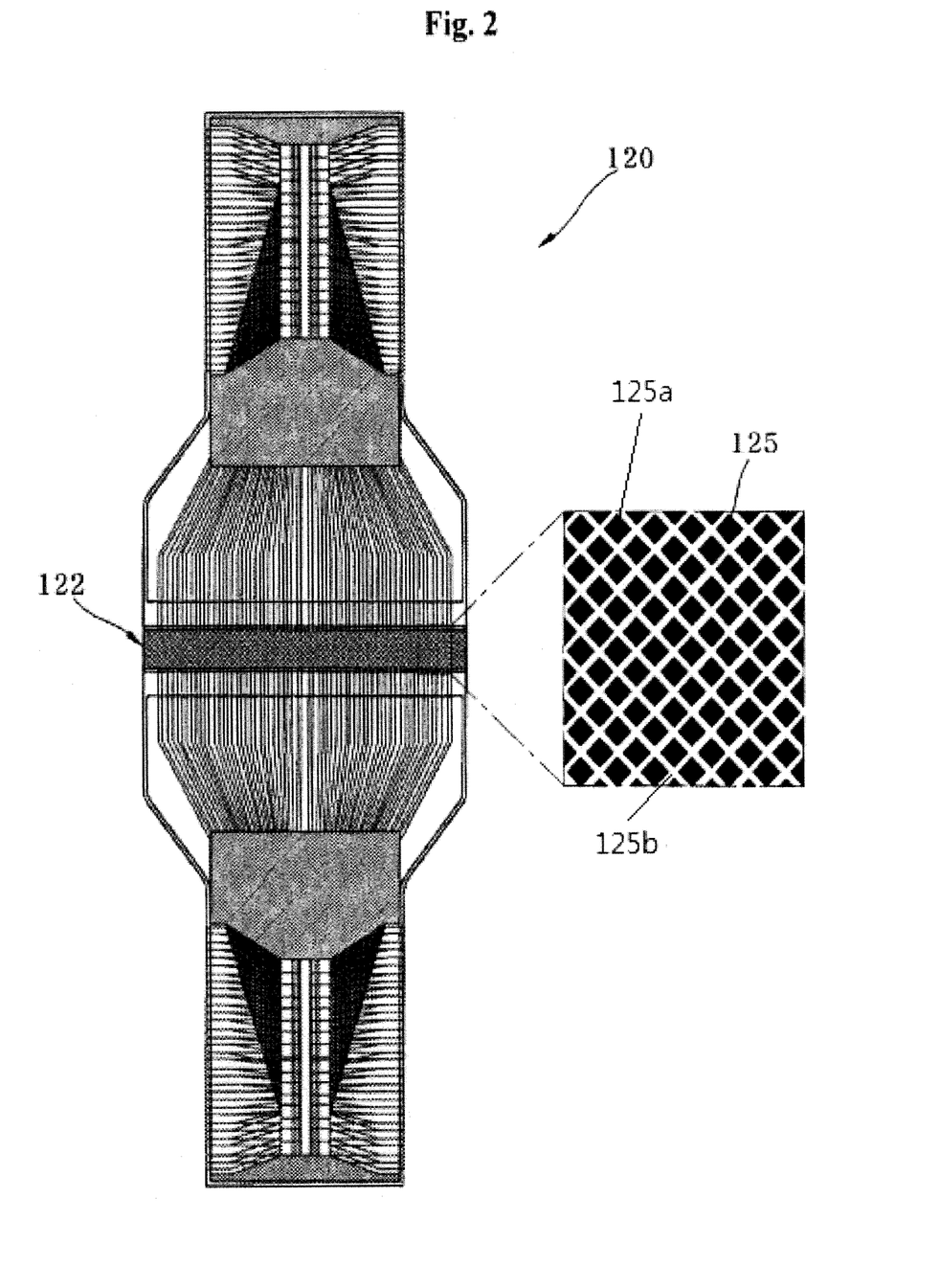
FIG. 2 is a view of a PCB shown in FIG. 1.

FIG. 1 is a schematic cross-sectional view of a probe according to an embodiment of the present invention, and FIG. 2 is a view of a PCB shown in FIG. 1.

Referring to FIGS. 1 and 2, a probe 100 according to the embodiment of the invention includes a transducer 110, a PCB 120, and a bonding member 130.

The transducer 110 transmits an ultrasound signal to a patient body and receives the ultrasound echo-sound reflected therefrom. The transducer 110 includes a piezoelectric layer 112 in which a piezoelectric material converts electrical signals to sound signals or vice versa while vibrating. The piezoelectric layer 112 includes a piezoelectric device 112a, which generates ultrasound waves through a resonance phenomenon, and signal and ground electrodes 112b and 112c provided to upper and lower ends of the piezoelectric device 112a, respectively.

The piezoelectric device 112a may be formed of a ceramic of lead zirconate titanate (PZT), a PZNT single crystal made of a solid solution of lead zinc niobate and lead titanate, a PZMT single crystal made of a solid solution of lead magnesium niobate and lead titanate, or the like. Further, the signal and ground electrodes 112b and 112c may be formed of a material having good electrical conductivity, such as gold, silver, or the like.

Further, the transducer 10 includes a coordination layer 114, which is formed of glass or resin materials and reduces a difference in sound impedance between the piezoelectric layer 112 and the patient body so as to allow as much of the ultrasound waves generated from the piezoelectric layer 112 to be transferred to the patient body as possible, a lens layer 116 focusing the ultrasound waves, which travel in front of the piezoelectric layer 112, onto a predetermined point, and a backing layer 118 blocking the ultrasound waves from traveling in a rearward direction of the piezoelectric layer 112 to prevent image distortion.

The PCB 120 is provided substantially perpendicular with respect to the lamination direction of the transducer 110. An example of the PCB 120 is a flexible printed circuit board (FPCB). The PCB 120 includes a bonding part 122 and a line electrode part 124.

The bonding part 122 contacts the piezoelectric layer 112 of the transducer 110, more specifically, a lateral side of the piezoelectric device 112a of the piezoelectric layer 112. The bonding part 122 includes a flexible electrical insulation film, and a metal layer formed on the electrical insulation film.

The line electrode part 124 includes a signal line electrode 124a and a ground line electrode 124b. The signal line electrode 124a and the ground line electrode 124b are disposed corresponding to the signal electrode 112b and the ground electrode 112c of the piezoelectric layer 112, respectively. The signal line electrode 124a and the ground line electrode 124b are soldered to the signal electrode 112b and the ground electrode 112c by a solder such as lead or the like, respectively, thereby electrically connecting the piezoelectric layer 112 to the PCB 120.

On the other hand, the bonding part 122 is bonded to the lateral side of the piezoelectric device 112a via a bonding member 130. The bonding member 130 is made of a non-conductive material to insulate the signal electrode 112b from the ground electrode 112c while bonding the piezoelectric device 112a to the bonding part of the PCB 120. The bonding member 130 may be an adhesive deposited between the bonding part 122 and the piezoelectric device 112a to form a bonding layer therebetween. Bonding between the bonding part 122 and the piezoelectric device 112a allows the PCB 120 to be bonded to the transducer 110.

The bonding part 122 is provided with a pattern part 125. The pattern part 125 is partially formed on the bonding part 122 or is formed over the entire surface of the bonding part 122. The pattern part 125 is provided to be in face-to-face contact with the piezoelectric layer 112 when the PCB 120 is bonded to the piezoelectric layer 112. The pattern part 125 is formed by etching the metal layer formed on the electrical insulation film of the bonding part 122 such that the electrical insulation film can be exposed in a predetermined shape.

According to this embodiment, the pattern part 125 is illustrated as including a predetermined pattern, more specifically, a rhombus pattern. The rhombus pattern may be formed in a convex portion 125a or a concave portion 125b on the bonding part 122. Here, the convex portion 125a corresponds to a portion where the metal layer is formed, and the concave portion 125b corresponds to a portion where the electrical insulation film is exposed.

In the probe 100 of this embodiment, the pattern part 125 is provided to the bonding part 122 of the PCB 120 bonded to the piezoelectric device 112a, as described above, so that the bonding part 122 has an increased bonding area and the bonding member 130 can come into contact with not only the metal layer of the bonding part 122 but also the electrical insulation film thereof, thereby enhancing the bonding force between the transducer 110 and the PCB 120.

In the probe 100 according to this embodiment, the transducer 110 and the PCB 120 can be more reliably bonded to each other, thereby preventing performance deterioration of the probe 100, which can be caused by defective connection between the transducer 110 and the PCB 120.

In the above description, the pattern part 125 is illustrated as including the rhombus pattern, but the present invention is not limited thereto.

FIGS. 3 to 7 are views of PCBs according to various embodiments of the present invention.

For convenience of description, the same or similar configurations as those of the above embodiment will be indicated by the same reference numerals, and detailed descriptions thereof will be omitted herein.

Figure 3:
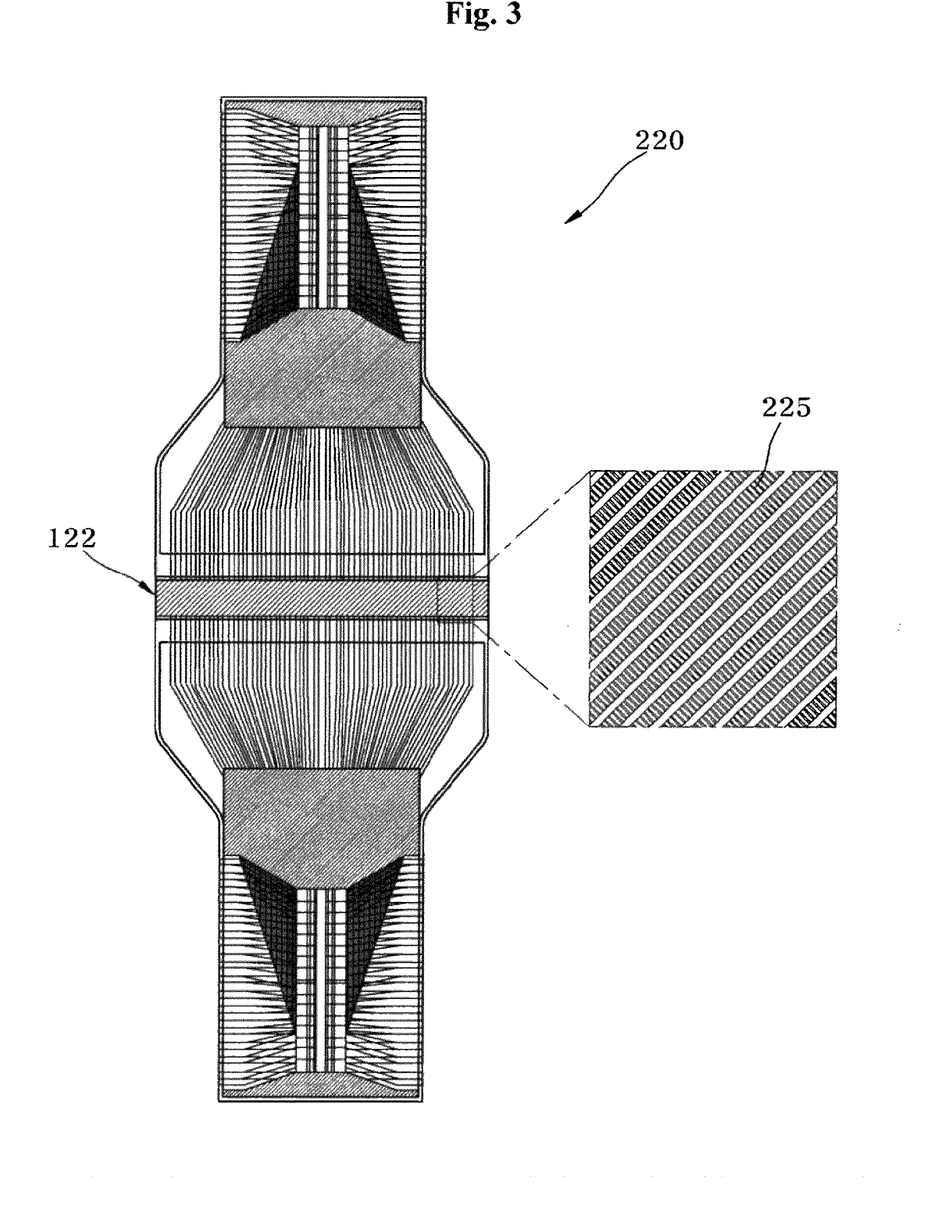
FIGS. 3 to 7 are views of PCBs according to various embodiments of the present invention.
Figure 4:
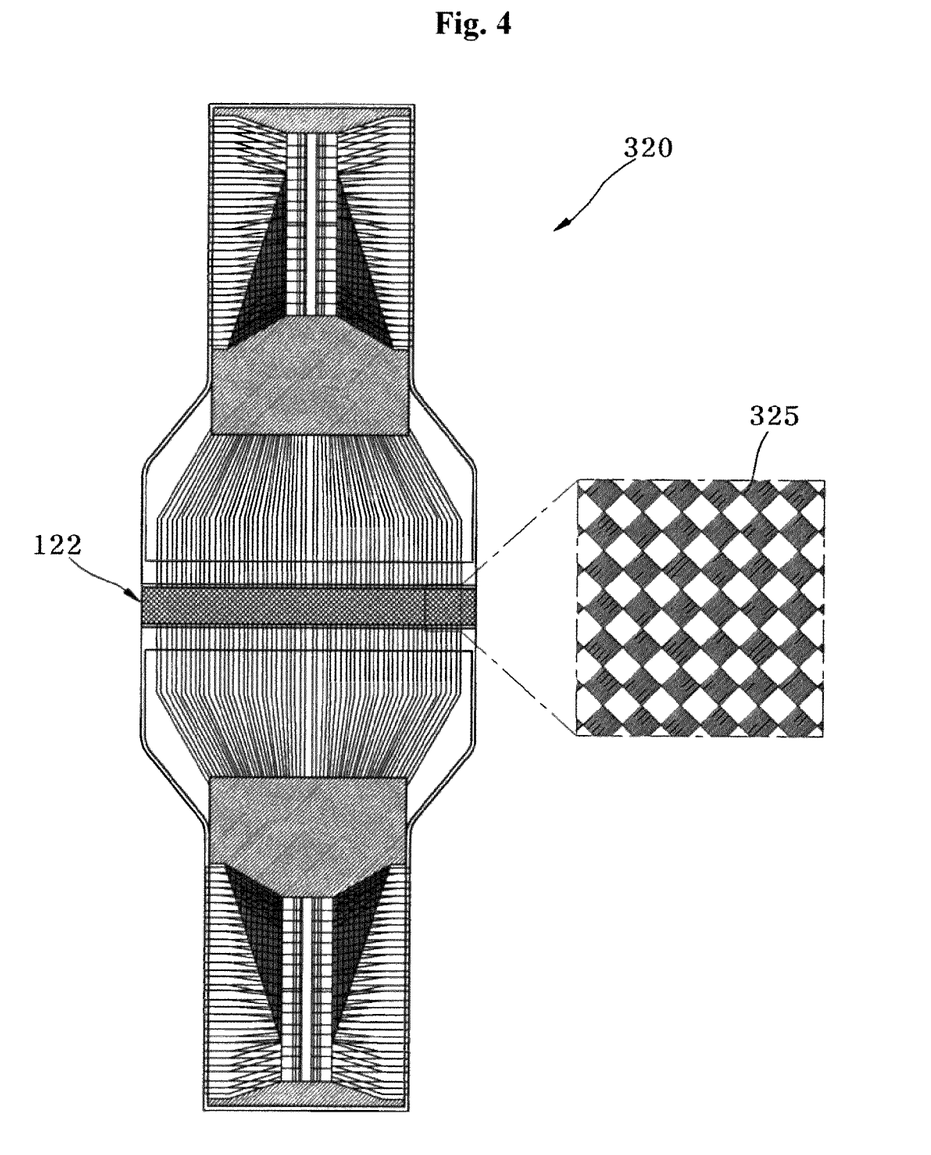
Figure 5:
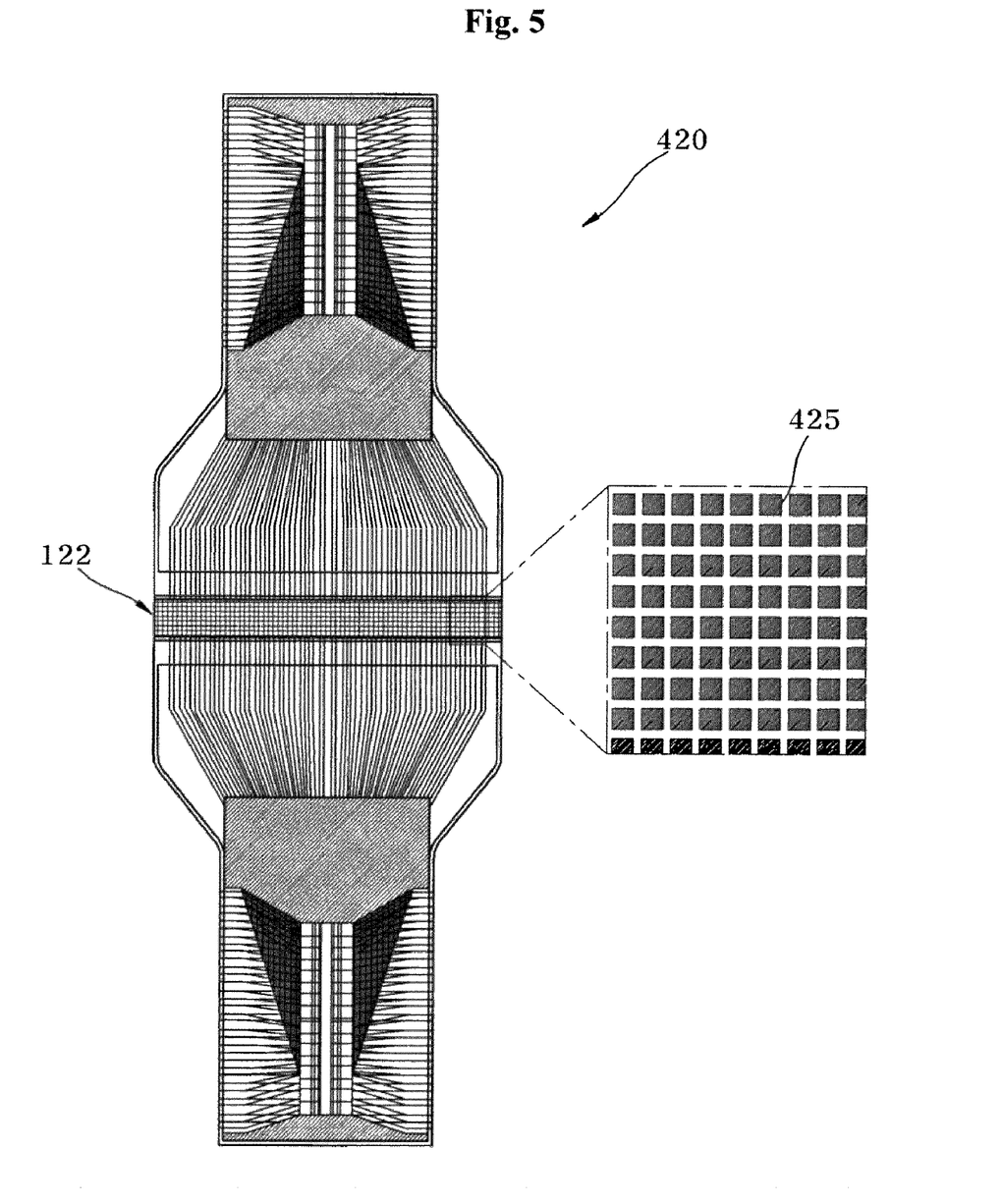
Figure 6:
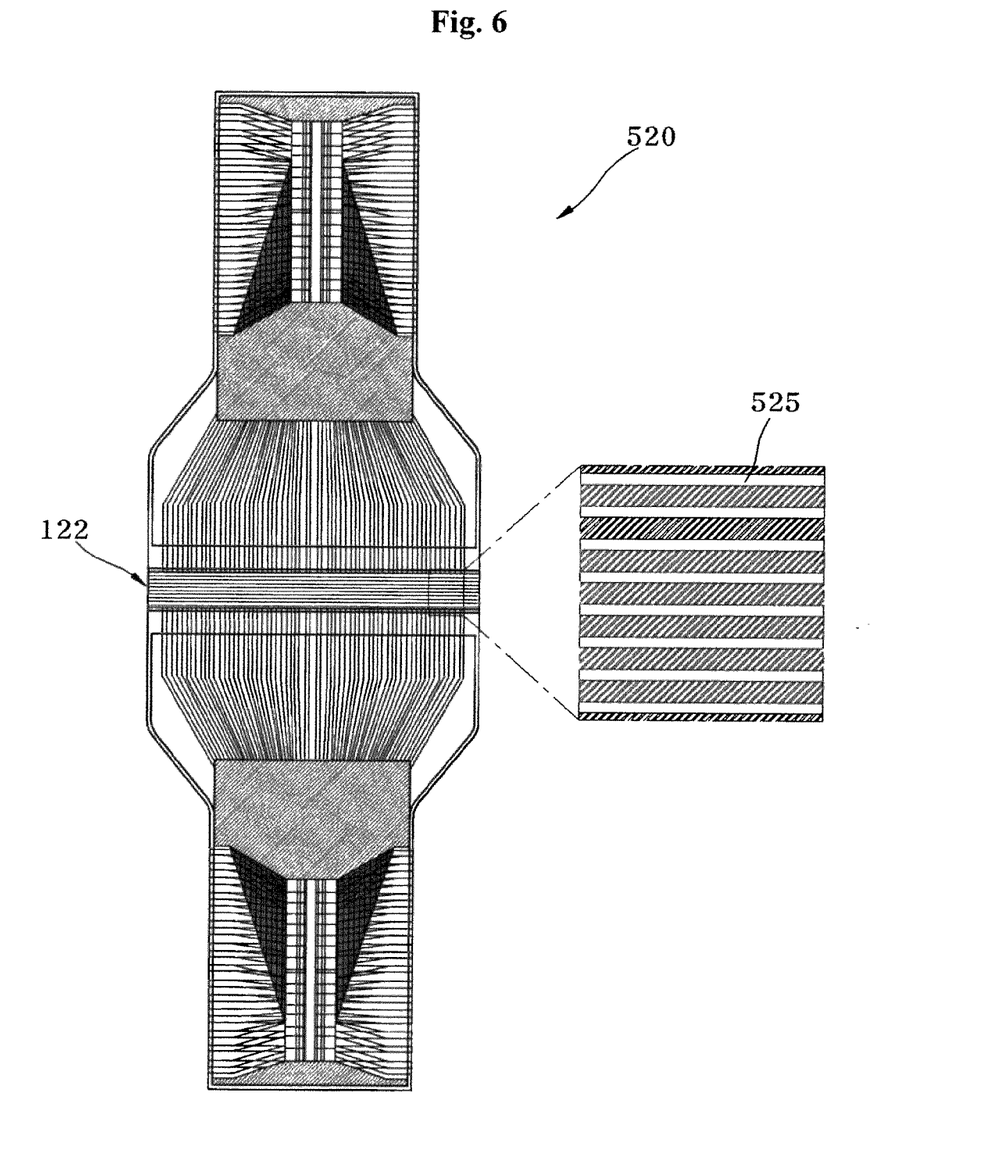
Figure 7:
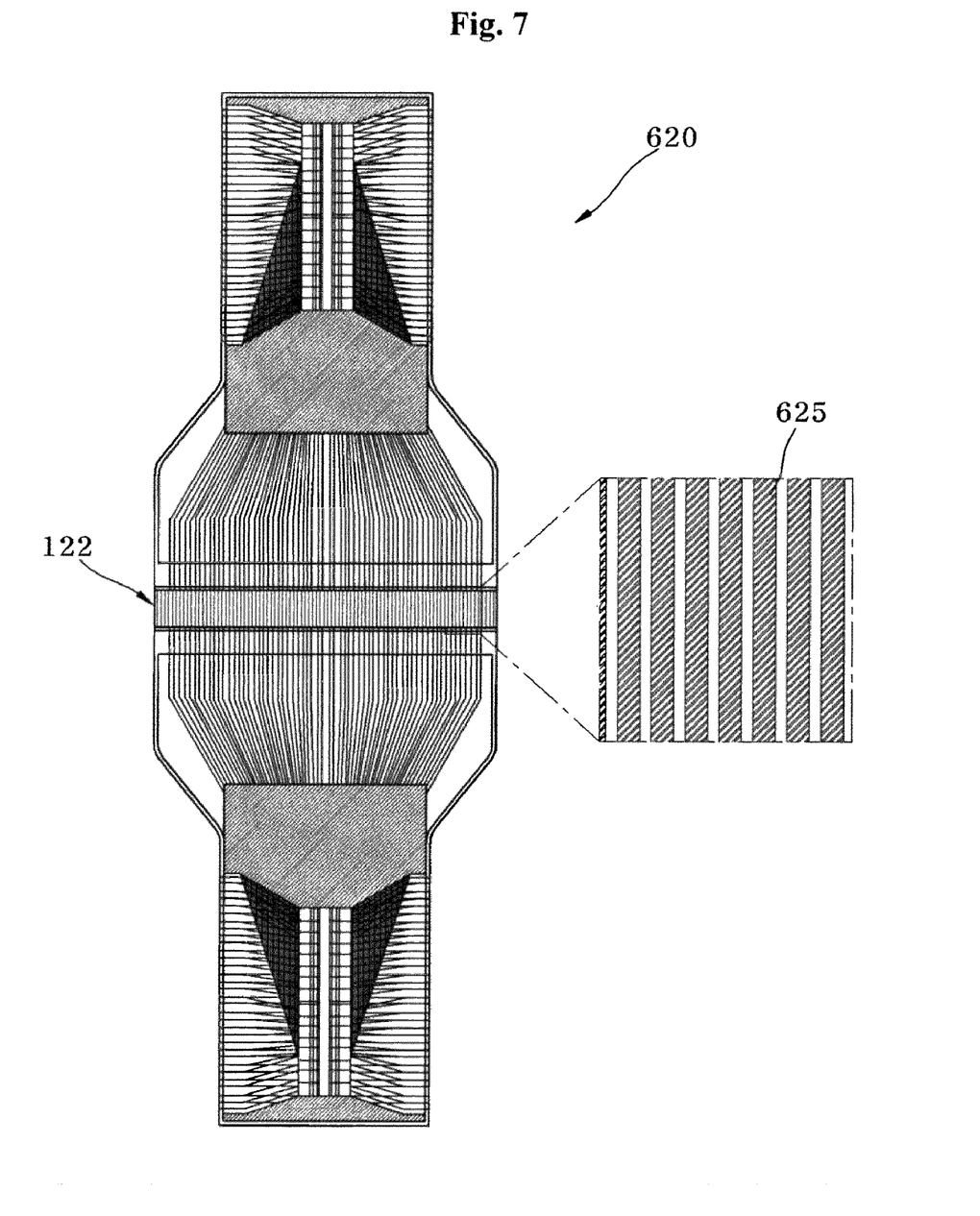

Referring to FIGS. 3 to 7, PCBs 220, 320, 420, 520 and 620 may have a pattern part 225 including an oblique line pattern as shown in FIG. 3, a pattern part 325 including a polygonal pattern of a rhombus shape as shown in FIG. 4, a pattern part 425 including a polygonal pattern of a rectangular shape as shown in FIG. 5, a pattern part 525 including a transverse line pattern as shown in FIG. 6, and a pattern part 625 including a lengthwise line pattern as shown in FIG. 7, respectively. Additionally, although not shown in the drawings, the pattern part may be realized in various modifications including a circular pattern, an elliptical pattern, a wave pattern, and the like.

Figure 8:
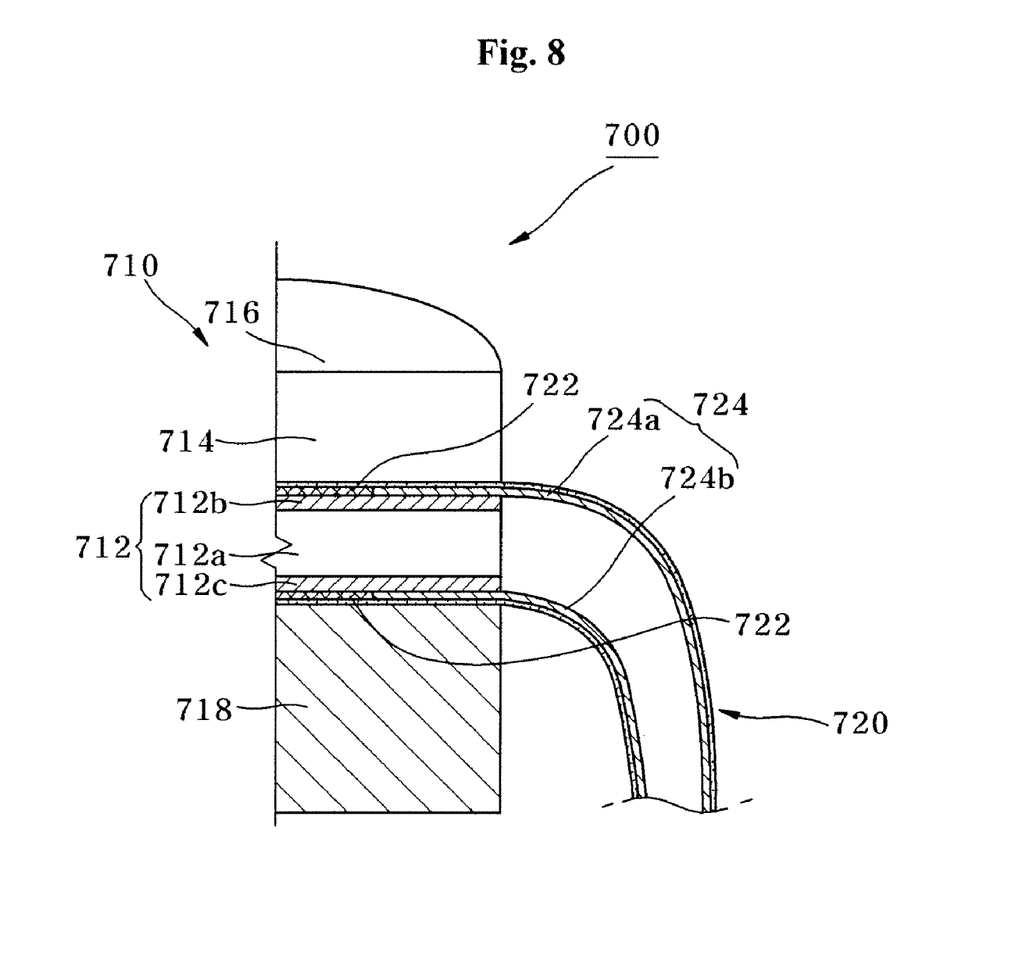
FIG. 8 is a schematic cross-sectional view of a probe according to another embodiment of the present invention.

FIG. 8 is a schematic cross-sectional view of a probe according to another embodiment of the present invention.

Referring to FIG. 8, a probe 700 according to this embodiment includes a transducer 710 and a PCB 720.

In FIG. 8, the transducer 710 includes a piezoelectric layer 712, a coordination layer 714, a lens layer 716, and a backing layer 718. The piezoelectric layer 712, coordination layer 714, lens layer 716, and backing layer 718 are stacked to constitute a laminate. The configuration and operation of the transducer 710 are similar to those of the transducer 110 (see FIG. 1) according to the above embodiment, and a detailed description thereof will be omitted.

The PCB 720 is provided substantially in the horizontal direction with respect to the lamination direction of the transducer 710, and includes a bonding part 722 and a line electrode part 724.

The bonding part 722 contacts an upper or lower side of a piezoelectric layer 712. The bonding part 722 includes a flexible electrical insulation film, and a metal layer formed on the electrical insulation film.

The line electrode part 724 includes a signal line electrode 724a and a ground line electrode 724b. The signal line electrode 724a and the ground line electrode 724b are disposed corresponding to a signal electrode 712b and a ground electrode 712c of the piezoelectric layer 712, respectively. The signal line electrode 724a and the ground line electrode 724b are soldered to the signal electrode 712b and the ground electrode 712c by a solder such as lead or the like, respectively, thereby electrically connecting the piezoelectric layer 712 to the PCB 720.

On the other hand, the bonding part 722 is bonded to the upper or lower side of the piezoelectric layer 712 via a bonding member (not shown). The bonding member bonds the bonding part 722 of the PCB 720 to the piezoelectric layer 712. The bonding member may be a non-conductive adhesive deposited between the bonding part 722 and the piezoelectric layer 712 to form a bonding layer therebetween. Bonding between the bonding part 722 and the piezoelectric layer 712 allows the PCB 720 to be bonded to the transducer 710.

The bonding part 722 is provided with a pattern part (reference numeral omitted). The pattern part is partially formed on the bonding part 722 or is formed over the entire surface of the bonding part 722. The pattern part is provided to be in face-to-face contact with the piezoelectric layer 712 when the PCB 720 is bonded to the piezoelectric layer 712. The pattern part is formed by etching the metal layer formed on the electrical insulation film of the bonding part 722 such that the electrical insulation film of the bonding part can be exposed in a predetermined shape. The configuration and operation of the pattern part are similar to those of the pattern parts 125, 225, 325, 425, 525 and 625 shown in FIGS. 2 to 7, and a detailed description thereof will be omitted herein.

As apparent from the above description, according to the embodiment of the present invention, a bonding part of the PCB is provided with a pattern part to increase a bonding area of the bonding part and to allow a bonding member to contact not only a metal layer of the bonding part but also an electrical insulation part, thereby improving a bonding force between a transducer and the PCB. As a result, the transducer can be reliably bonded to the PCB, so that performance of the transducer can be prevented from being deteriorated due to defective connection between the PCB and the transducer.

Although the present invention has been described with reference to the embodiments shown in the drawings, it will be apparent to those skilled in the art that the embodiments are given by way of illustration only, and that various modifications and equivalent embodiments can be made without departing from the spirit and scope of the present invention. Accordingly, the scope of the present invention should be limited only by the accompanying claims.

What is claimed is:

1. A probe comprising:
   a transducer comprising a piezoelectric element to generate ultrasound waves, a signal electrode formed on an upper surface of the piezoelectric element, and a ground electrode formed on a lower surface of the piezoelectric element;
   a printed circuit board (PCB) comprising a bond part having a pattern part surface-contacting the transducer, a signal line electrode electrically connected to the signal electrode, and a ground line electrode electrically connected to the ground electrode; and
   a bonding member bonding the transducer to the pattern part of the PCB,
   wherein the bonding part is bonded to a lateral side of the piezoelectric element via the bonding member.

2. The probe according to claim 1, wherein the pattern part comprises at least one of a polygonal pattern, a transverse line pattern, a lengthwise line pattern, an oblique line pattern, a circular pattern, an elliptical pattern, and a wave pattern.

3. The probe according to claim 1, wherein the pattern part comprises a convex portion.

4. The probe according to claim 1, wherein the pattern part comprises a concave portion.

* * * * *